(12) United States Patent
Briman et al.

(10) Patent No.: US 8,988,079 B2
(45) Date of Patent: *Mar. 24, 2015

(54) CARBON-BASED ELECTRODES WITH GRAPHENE MODIFICATION

(71) Applicant: Proxim Diagnostics, Sunnyvale, CA (US)

(72) Inventors: Mikhail Briman, Sunnyvale, CA (US); Vikram Joshi, Santa Monica, CA (US)

(73) Assignee: Proxim Diagnostics, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/267,914

(22) Filed: May 2, 2014

(65) Prior Publication Data

US 2014/0242262 A1 Aug. 28, 2014

Related U.S. Application Data

(63) Continuation of application No. 13/517,471, filed as application No. PCT/US2010/061503 on Dec. 21, 2010, now abandoned.

(60) Provisional application No. 61/290,130, filed on Dec. 24, 2009.

(51) Int. Cl.
*G01N 27/02* (2006.01)
*G01N 27/30* (2006.01)
*H01B 1/04* (2006.01)
*G01N 27/327* (2006.01)

(52) U.S. Cl.
CPC ............... *G01N 27/308* (2013.01); *H01B 1/04* (2013.01); *G01N 27/3275* (2013.01)
USPC .......................................................... 324/446

(58) Field of Classification Search
CPC ...... G01N 27/308; G01N 27/3275; H01B 1/04
See application file for complete search history.

(56) References Cited

U.S. PATENT DOCUMENTS 5,324,400 A * 6/1994 Eliash et al. ................... 205/794
2009/0159464 A1 * 6/2009 Hyland et al. ................. 205/790

OTHER PUBLICATIONS

Bleda-Martinez, et al., Electrochemical Methods to Enhance the Capacitance in Activated Carbon/Polyaniline Composites, Journal of The Electrochemical Society, 155 (10) 1-XXXX (2008).*

(Continued)

*Primary Examiner* — Melissa Koval
*Assistant Examiner* — Daniel Miller
(74) *Attorney, Agent, or Firm* — Jeffrey Jue; Catalyst IP Group

(57) ABSTRACT

Certain embodiments of the present application describe a carbon-based electrode with graphene platelets. The addition of graphene platelets is intended to improve properties of the electrode. These properties include, but are not limited to, physical, electrical, and biochemical properties of the electrode. Enhanced reproducibility of these properties can also result from the addition of the graphene platelets.

19 Claims, 8 Drawing Sheets

(56) References Cited

OTHER PUBLICATIONS

Nian, et al., Nitric Acid Modification of Activated Carbon Electrodes for Improvement of Electrochemical Capacitance, Journal of The Electrochemical Society, 149 (8) A1008-A1014 (2002).*

Ranganathan, et al., Facile Preparation of Active Glassy Carbon Electrodes with Activated Carbon and Organic Solvents, Anal. Chem., 71, 3574-3580 (1999).*

Anjo, et al., Electrochemical activation of carbon electrodes in base: minimization of dopamine adsorption and electrode capacitance, Anal. Chem., 1989, 61 (23), pp. 2603-2608.*

* cited by examiner

| Measurement | Graphene Modified Sensor Positive Control | Graphene Modified Sensor Negative Control | Unmodified Sensor Positive Control | Unmodified Sensor Negative Control |
| --- | --- | --- | --- | --- |
| | I (nA) | I (nA) | I (nA) | I (nA) |
| 1 | 1483.73 | 2.551 | 1178.838 | 3.013 |
| 2 | 1389.901 | 2.394 | 1173.585 | 2.572 |
| 3 | 1373.331 | 2.298 | 1168.272 | 2.385 |
| 4 | 1189.35 | 2.139 | 1115.011 | 2.258 |

CARBON-BASED ELECTRODES WITH GRAPHENE MODIFICATION

This application is a continuation application of U.S. patent application Ser. No. 13/517,471, filed Jun. 20, 2012 and entitled "CARBON-BASED ELECTRODES WITH GRAPHENE MODIFICATION," which claims priority to PCT Application No. PCT/US2010/061503, filed Dec. 21, 2010 and entitled "CARBON-BASED ELECTRODES WITH GRAPHENE MODIFICATION," and U.S. Provisional Application No. 61/290,130, filed Dec. 24, 2009 and entitled "CARBON-BASED ELECTRODES WITH GRAPHENE MODIFICATION," all of which are hereby incorporated herein by reference.

FIELD OF THE INVENTION

The present invention relates generally to carbon-based electrodes that are modified by graphene platelets.

BACKGROUND OF THE INVENTION

In electrochemistry, the performance of the working electrode in a sensor is of prime importance. In electrochemical sensor applications, the electrode of choice often consists of a carbon-based material.

Graphene platelets are a material that has nano-scale size, high conductivity, and a chemical resemblance to traditional graphite. Certain processes to form graphene platelets and formulate into ink are known in the art.

Sensors with carbon-based electrodes have then been used to detect analytes such as glucose and dopamine. However, use of carbon-based electrodes in sensors is held back by the magnitude and lack of reproducibility of the electrochemical response. The electrode's exposed surface materials, roughness and other critical properties are most responsible for the poor sensor behavior.

SUMMARY OF THE INVENTION

The present invention describes a material that modifies a carbon-based electrode. For biological and chemical sensing applications, the carbon-based electrode is the transducer element of the electrochemical sensor. As used herein, a "carbon-based" electrode may include, but is not limited to, one that is a glassy carbon, pyrolytic carbon film(s) and/or screen printed electrode(s), and/or any basic electrode composed of graphene, carbon black, carbon particles, carbon nanotubes, graphite, and/or other form of carbon that can be electrically conductive.

Certain embodiments of the present invention may improve the electrochemical characteristics of the carbon-based electrode. This improvement may take the form of greater electrochemical activity and greater overall conductivity of the electrode. Additionally, the modification may enhance the overall efficiency of the electron transduction process whereby the electrode is used in an electrochemical process such as sensing.

Certain embodiments of the present invention may improve the surface properties of the carbon-based electrode. Because the modification can result in a surface morphology that has a feature size comparable with the size scale of various biological molecules (for example, IgG antibodies), the coverage or packing density as well as coverage uniformity of the electrode surface would be augmented. Using the electrode as part of an electrochemical sensor, the better packing density and uniformity can translate ultimately to greater sensitivity in measurement.

Certain embodiments may provide advantage over alternate modification methods in regards to the reproducibility of the carbon-based electrode in its physical, electrical and biochemical properties. The result of the present invention may be that a group of electrodes modified with graphene platelets would have a narrower distribution in their physical, electrical, and biochemical properties when compared to a group of conventional carbon-based electrodes (i.e., that are not modified by graphene platelets).

Electrodes modified with graphene platelets, according to certain embodiments of the present invention, may display improved electrochemical properties (as compared to conventional carbon-based electrodes) including, but not limited to, lower nonspecific binding of biomolecules, increased signal-to-noise ratio, lower detection limits and higher electrochemical activity.

Other features and advantages of the invention will be apparent from the accompanying drawings and from the detailed description. One or more of the above-disclosed embodiments, in addition to certain alternatives, are provided in further detail below with reference to the attached figures. The invention is not limited to any particular embodiment disclosed; the present invention may be employed in not only sensor applications, but in other applications as well.

BRIEF DESCRIPTION OF THE DRAWINGS

The invention is better understood from reading the following detailed description of the preferred embodiments, with reference to the accompanying figures in which:

FIG. 5 is a table showing the response of graphene modified electrodes and unmodified electrodes acting as immunological sensors under exposure to thyroid stimulating hormone in positive and negative control conditions.

Features, elements, and aspects of the invention that are referenced by the same numerals in different figures represent the same, equivalent, or similar features, elements, or aspects in accordance with one or more embodiments of the system.

Those of ordinary skill in the art will appreciate that features, elements and aspects of the invention depicted in the figures in a similar or identical manner may be similar or identical, even if, for example, a plurality of such features, elements and aspects are not individually labeled.

DETAILED DESCRIPTION OF THE EMBODIMENTS

Figure 1:
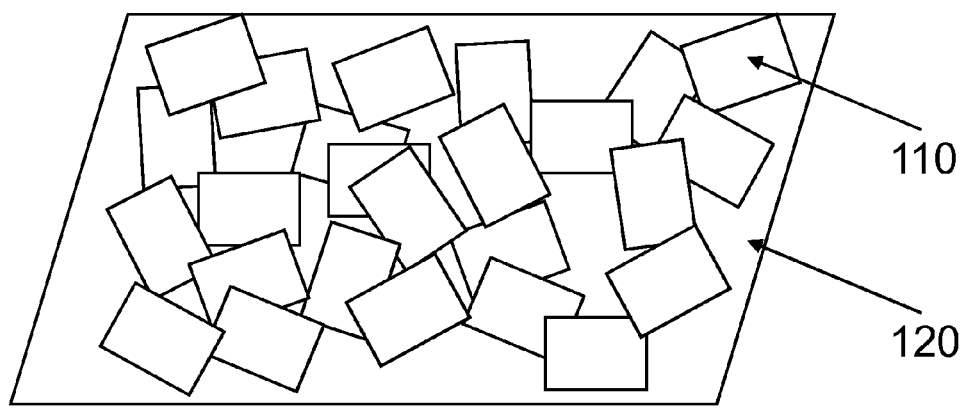
FIG. 1 is a drawing depicting a film, according to certain embodiments of the present invention, having at least one monolayer of graphene platelet material with some overlap between individual platelets.

The invention primarily comprises modifications of carbon-based electrodes in various arrangements with graphene platelets. A graphene platelet is a nano-scale flake of graphene, which may have a thickness ranging from a monolayer to many monolayers. Referring to FIG. 1, the graphene platelets 110 can be arranged onto a surface 120 to form a layer of material. There may be overlap between adjacent graphene platelets to maintain an electrically conducting pathway through the layer of material.

Such modification of a carbon-based electrode with graphene platelets may alter the electronic properties, surface properties, and/or reproducibility of the carbon-based electrode.

Graphene platelets, for example as described above, can provide a sensitive transduction layer, e.g., where the electrochemical activity of the layer is high. The electrical conductivity of the interconnected graphene platelets may be higher than that of the carbon-based electrode (without graphene functionalization), and this increased conductivity can lead to better electron transduction. For the example of screen printed sensors, the electrons generated by captured or electrochemically-labeled biomolecules would be more efficiently transduced and detected, yielding greater sensitivity, i.e., ability to detect lower concentrations of analytes.

Graphene modification according to embodiments of the present invention may also smooth the surface of a carbon-based electrode, e.g., where graphene flakes having nanoscale dimensions fill gaps (holes, pores, channels, unevenness, etc.) in a carbon-based electrode comprised of relatively larger structured forms of carbon (e.g., graphite). This smoothing effect can significantly improve application (e.g., sensor properties). For example, smoothing of the electrode surface can make the surface more amenable to sensor molecule attachment, allowing improved, more reliable and/or more uniform attachment; and thereby increasing sensitivity and/or decreasing variability in sensor applications. In addition to smoothing the surface, graphene modification can increase the surface area of a carbon-based electrode (e.g., due to graphene flakes' nanoscale dimensions). In one embodiment of the present invention, graphene modified electrodes allow greater attachment of antibodies and/or DNA onto the electrode surface, and corresponding greater capture of target molecules.

In addition to the structural effects of graphene modification, graphene can be chemically more amenable to sensor molecule attachment than other materials in the carbon-based electrode (e.g., due to functionalization at the edges of graphene flakes). In certain embodiments of the present invention, antibodies can be attached to the electrode surface via adsorption or through carbon chemistry to covalently attach them to the graphene layer. There may further be an advantage due to more carboxyl groups on the graphene surface for this covalent attachment of the antibodies.

Because of the aforementioned electrical effect, structural effect and smoothing effect of graphene modification according to embodiments of the present invention, such graphene modification can narrow the distribution and variability in a carbon-based electrode's surface, electronic, chemical properties. Hence, the electrodes modified with graphene according to the present invention would be more reproducible—important not only for functionality, but also for manufacturability.

First Embodiment

Top Layer

For the first embodiment, there exists a base electrode layer that is composed of some amount of carbon-based material that sits atop a substrate. On top of the base electrode layer is a top layer of graphene platelets that may be in combination with a binder.

Figure 2:
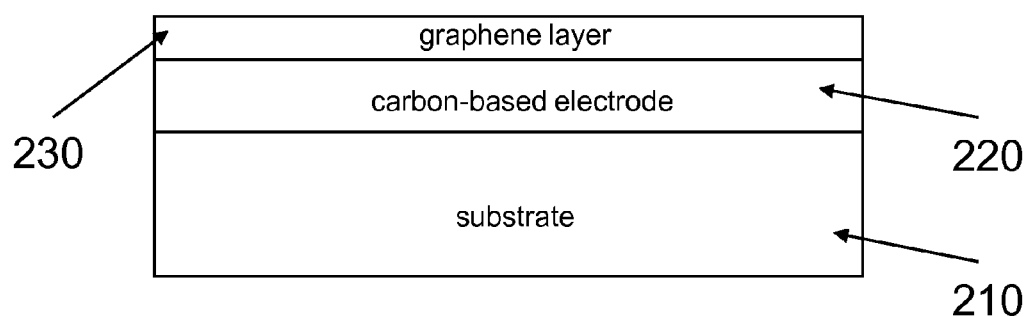
FIG. 2 is a schematic of an electrode, according to certain embodiments of the present invention, wherein the top layer is comprised of graphene platelets (labeled "graphene layer").

Referring to FIG. 2, the entire structure may be formed atop a substrate 210. A carbon-based electrode is the base layer 220. The graphene layer may then be deposited as to be the top layer 230.

The top layer can thus modify the base electrode layer and would be at least one monolayer in thickness. The effective structure setup such that the top layer is would be exposed to the environment. The top layer may or may not be continuous in all places.

An electrode apparatus according to certain embodiments of the present invention comprised an 8 pad electrode screen-printed sensor ("8-plex device"). This device was employed to demonstrate improvement of the electrochemical properties of the electrode and witness the performance effects of the electrode acting as an immunological sensor after graphene modification of the electrode.

Figure 3A:
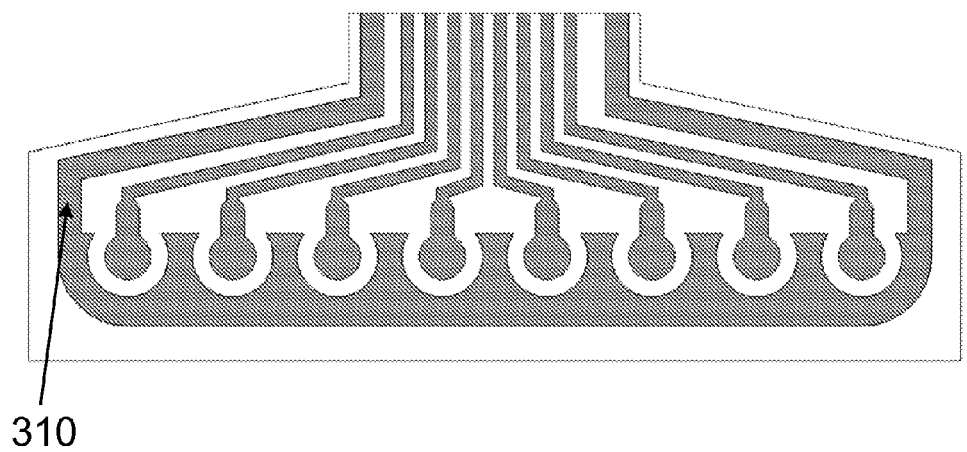
FIGS. 3A-3E are schematic representations of an electrode apparatus and device fabrication process according to certain embodiments of the present invention, wherein top layer modification by graphene is employed.

Referring to FIG. 3A, the 8-plex device may be fabricated by first screen-printing silver ink contact traces 310 on a plastic flexible substrate.

Figure 3B:
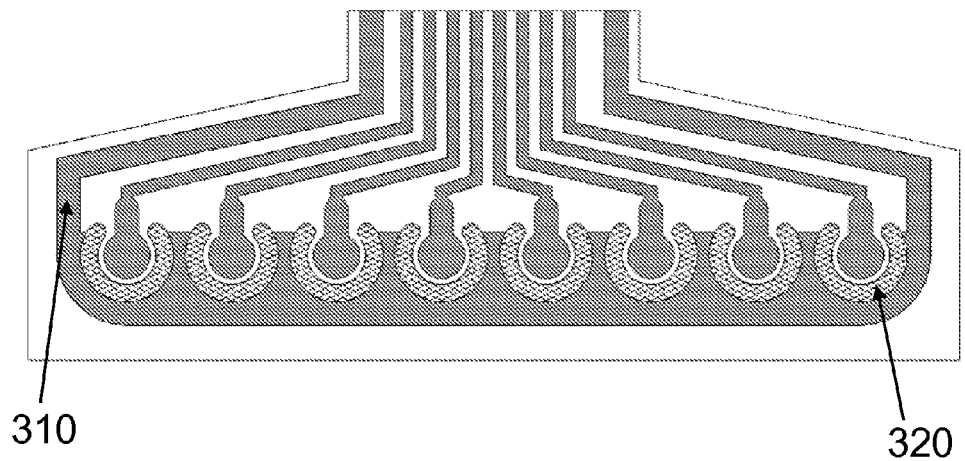

Referring to FIG. 3B, silver/silver chloride (Ag/AgCl) inks may then be screen-printed to form a reference electrode 320.

Figure 3C:
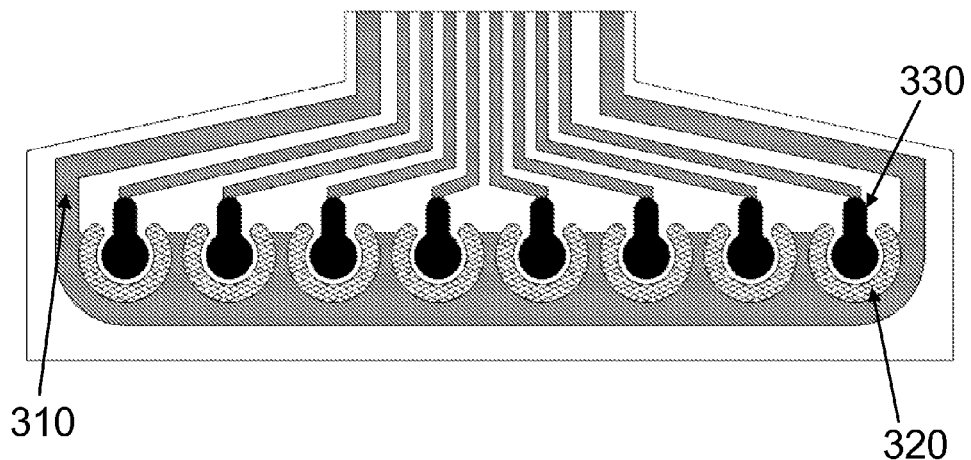

Referring to FIG. 3C, carbon inks (e.g., proprietary inks) may then be screen-printed to form 8 sensors (working electrodes, sensor electrodes) 330.

Figure 3D:
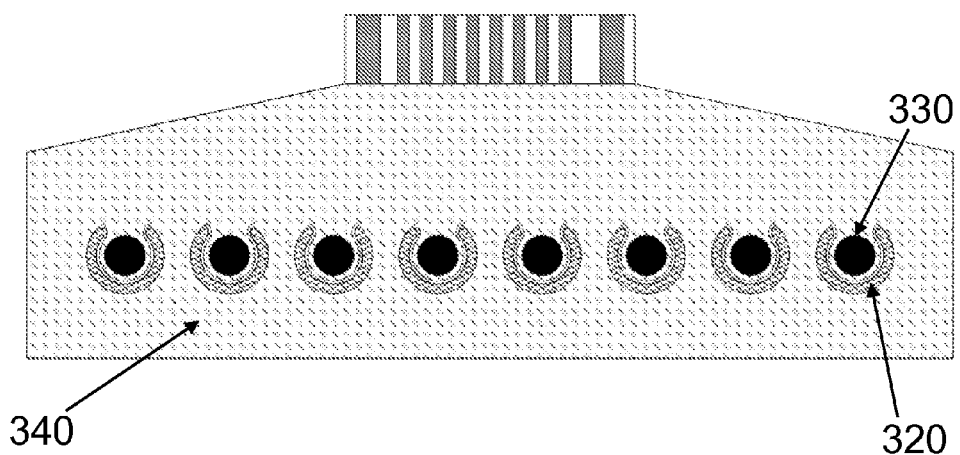

Referring to FIG. 3D, an insulation layer 340 may then be screen-printed, for example, to have only carbon sensing pads and reference electrodes be exposed to liquid.

Figure 3E:
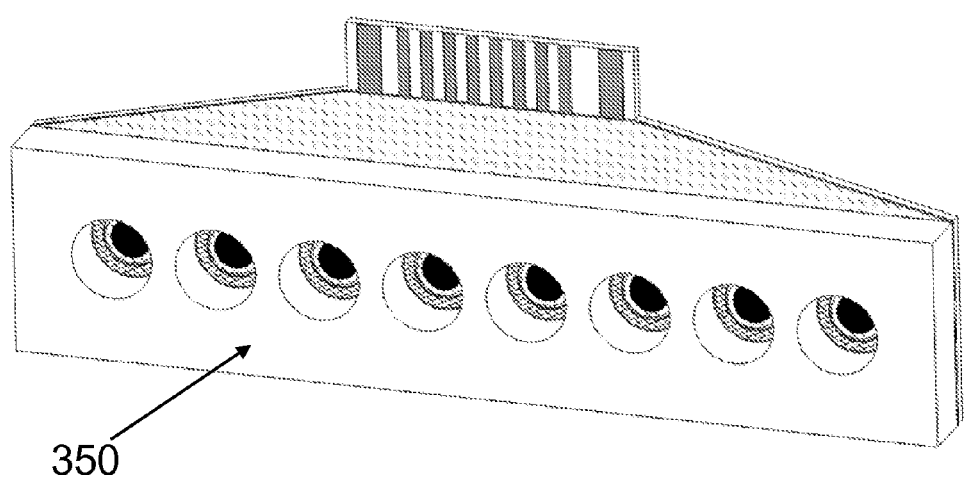

Referring to FIG. 3E, a plastic top part 350 with 8 openings may then be glued on top of the plastic to form 8 isolated wells for liquid application.

Electrode apparatuses, e.g., 8-plex devices as described above, according to certain embodiments of the present invention may be connected to an electronic measuring setup that allows setting the user-defined voltage V (V) on the reference electrode and measuring individual pad currents I (A).

The 8-plex device may be modified by graphene in the following method. The 8-plex device may be placed on a heated surface at 50 C. Then a solution of graphene ink that may consist of graphene platelets in ethanol may be drop-casted onto an individual sensor pad of an 8-plex device and may be repeated as to modify other pads. Some pads of the device may be left unmodified. The method may be used to deposit at least a single monolayer of graphene or many monolayers by controlling the number of drops deposited onto the sensor pad (note: the monolayer(s) may or may not be continuous in all places). In an experimental embodiment of the present invention, each modified pad had an average of 3 monolayers of graphene, i.e., the equivalent of 1 nm extra thickness was introduced onto the bare electrode surface.

Figure 4:
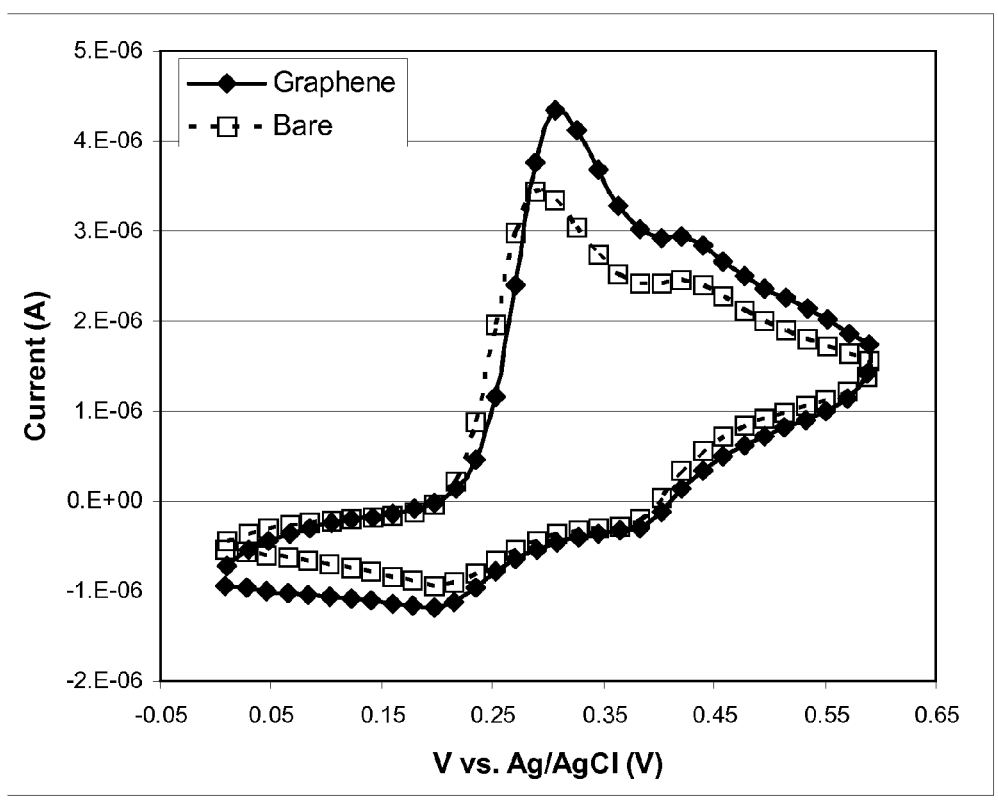
FIG. 4 is graph of the cyclic voltammetry plots for graphene-modified and bare electrodes under exposure to a tetramethylbenzidine (TMB) based aqueous buffer.

Referring to FIG. 4, the 8-plex device was measured by cyclic voltammetry to compare the effect of top layer graphene modification versus bare electrodes under exposure to Tetramethylbenzidine (TMB) based aqueous buffer (substrate). TMB is an electrochemically active substance that can be oxidized and reduced on carbon-based working electrodes at potentials ranging from approximately 0.2 to 0.5 V vs. Ag/AgCl reference electrode. TMB was selected because of its contribution to amperometric signal generation when employed in immunological sensors.

Analysis of the experiment, corresponding to certain embodiments of the present invention, shows a typical result comparing electrochemical performance of the graphene modified electrode and the bare carbon-based electrode in FIG. 4. It was observed that after graphene modification, the magnitude of oxidation and reduction currents increased by 26% and 27% respectively, indicating an improvement in electrochemical activity of electrode interaction with a TMB-based substrate. This change in activity would improve performance characteristics of chemical and biological sensors, in particular immunological sensors, that employ graphene-modified electrodes.

The graphene-modification procedure according to certain embodiments of the present invention, e.g. as described above, may be employed to improve properties of an immunological electrochemical biosensor that has carbon-based electrodes. The sample embodiment below describes a Thyroid Stimulating Hormone assay that served as a model system.

Construction of an Immunological Sensor

Immunological sensors according to certain further embodiments of the present invention were constructed on two 8-plex devices. First, 4 pads of an 8-plex device were modified with graphene, leaving the other 4 pads unmodified. Next, all 8 pads were covered with 30 µg/ml monoclonal anti-TSH (Thyroid Stimulating Hormone) capture antibodies in a proprietary coating buffer and left in a humidity chamber for 2 hours at room temperature. After this, the devices were rinsed twice with PBST (phosphate buffered saline+0.05% Tween 20) and covered with a proprietary protein blocking agent to cover areas on the sensor surface where no antibodies attached. After 1 hour of blocking at room temperature, the blocking agent was aspirated and devices were dried.

Two different detection analytes were prepared. The first consisted of protein-based buffer that contained 500 ng/ml anti-TSH antibodies labeled with HRP (horseradish peroxidase) to serve as detection antibodies. This analyte was designed to serve as negative control. The second analyte designed to serve as the test material (hereafter, positive control) was made exactly in the same manner as negative control, but in addition the analyte was spiked with TSH reference material to a concentration of 25 µIU/mL.

Of the sensor pads, 4 were exposed to the positive control, while another 4 pads were exposed to the negative control. The devices were put on a rotational shaker and were allowed to react with analyte for 30 minutes at room temperature. As is common with ELISA experiments, the positive control case, had antibodies on the electrode surface that would capture TSH from one side, and the detection antibodies would attach to the other side of TSH protein forming an antibody "sandwich" structure. In contrast, for the negative control case, the undesired non-specific binding of the reporter antibodies to the electrode surface would be present and no "sandwich" would be formed.

After 30 minutes of incubation, the 8-plex devices were washed several times with PBST to remove unbound analyte and detection antibodies. All pads were then exposed to TMB-based substrate that upon reaction with HRP labels on the reporter antibodies produces an electrochemically active species that is detected amperometrically by an electronic measurement of the device.

Referring to FIG. 5, the table displays sensor response for two 8-plex devices, 4 positive and 4 negative control signals on the graphene modified electrodes, as well as similar data points for unmodified electrodes. In the case of graphene-modified electrodes, the average of 4 positive control signals was 1359 nA, while the average of 4 negative controls was 2.35 nA, providing a signal-to-noise ratio was 579.4. For unmodified electrodes, the average positive and negative signals were 1159 nA and 2.56 nA, respectively. The signal-to-noise ratio here was 453.2. From the measurements, the graphene modification showed improvement in signal-to-noise ratio by approximately 28%. Therefore, electrode modification by graphene would result in greater sensitivity, which translates to improvement in the limit of detection for a given immunological sensor.

Further improvements in the graphene modification process described above may lead to even greater improvement in signal-to-noise ratio. And more automated and non-manual depositions methods for graphene ink may lead to reduced variability amongst the response of modified electrodes. Those of ordinary skill in the art will appreciate that the scope of the present invention is not limited to improvement levels described above (e.g., data from present experimental embodiments).

Second Embodiment

Multilayer Structure

For the second embodiment, a multilayer structure could provide more structural integrity, add functionality, provide conductivity, enhance electrochemical properties or be used as adhesion layer(s) for other carbon-based layers. Any number of layers or composite layers could be used. In particular, multiple layers of graphene could be incorporated adjacent to other material layers. Alternatively, the multilayer structure could be exclusively made up of graphene platelets whereby it is built up layer by layer. For this structure, there would be at least one graphene layer with a minimum thickness of a monolayer (note: the monolayer(s) may or may not be continuous in all places).

Figure 6:
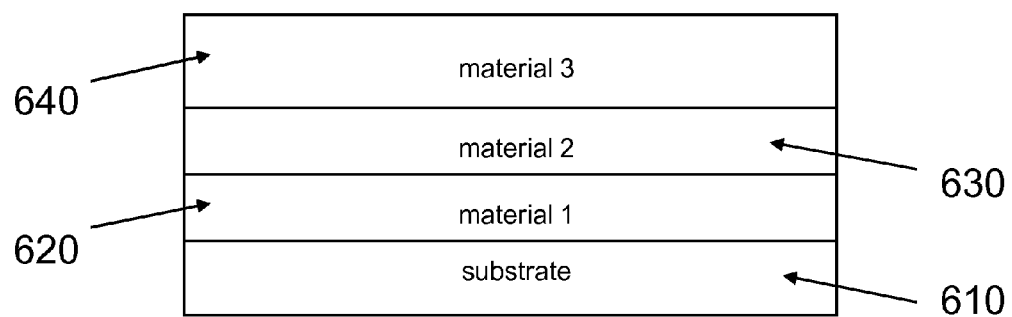
FIG. 6 is a schematic of an electrode, according to certain embodiments of the present invention, having a multi-layer structure wherein at least one layer of the assembly is comprised of graphene platelets.

Referring to FIG. 6, carbon layers may sit atop a substrate 610. For the next layers 620, 630, and 640, at least one layer may comprise graphene platelets and at least one layer may be a carbon-based electrode. Other layers may comprise other materials that may include polymers, small molecules, biological molecules, metals, ceramics, or nanostructured materials in the form of wires, particles, flakes, etc.

For example, one may start with a graphene ink as stated above and other materials that may be assembled into a multilayer structure. For this example, the base electrode layer may be screen printed carbon on top of a plastic substrate. Then layers of other materials consisting of polymers, metal nanoparticles, carbon micro/nanostructures, including graphene or the like, may be constructed on top of each other. The top layer 640 may be composed of graphene platelets.

Third Embodiment

Composite Electrode

For the third embodiment, a composite material is used to form the entirety of the carbon-based electrode. The composite electrode would primarily start with a recipe for that of a conventional carbon-based electrode. The composite material would encompass any ratio of materials that involves some amount of the graphene nanoplatelets. The other material components may be other carbon micro/nanomaterials, metals, inorganics, or organic species.

Figure 7:
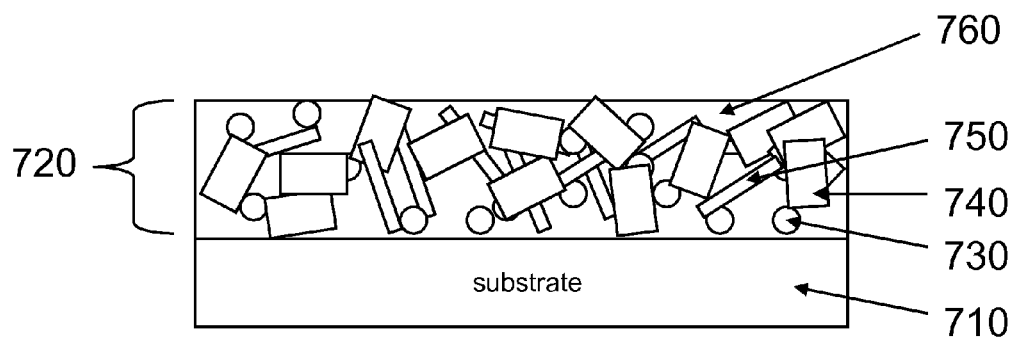
FIG. 7 is a schematic of an electrode, according to certain embodiments of the present invention, comprised of a composite of various materials, one of which is graphene nanoplatelets.

Referring to FIG. 7, the composite electrode sits atop a substrate 710. The electrode 720 comprises various materials, e.g., nanoparticles 730, graphene platelets 740, and/or nanorods/nanotubes 750 in a matrix 760 that binds the assembly together.

For example, one can form this composite by establishing an ink formulation consisting of at least graphite and graphene platelets, solvent, and a binder. Additionally, other non-carbon materials may be used such as metal nanoparticles. This ink or paste would then be deposited, e.g., through a screen printed process, to form the composite electrode on top of the substrate.

Fourth Embodiment

Deposition Techniques for Graphene Layer Formation

In certain embodiments of the present invention, various techniques may be used in the formation of the structures described above. In a typical format, the graphene platelets are part of an ink. This ink is then deposited through a given method to form a film with the intent of placement onto a substrate or a material layer of interest. The various ink deposition methods may include but are not limited to spray painting, drop casting, spin coating, vacuum filtration, dip coating, screen printing, and ink-jet printing. Certain methods may provide droplet size or other conditions that lead to ultra-thin layers, greater uniformity of films, and control of surface and thickness parameters.

Figure 8:
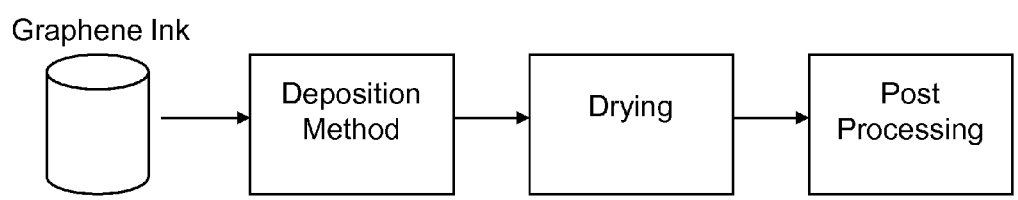
FIG. 8 is a flow chart of a general process, according to certain embodiments of the present invention, that may be used to fabricate carbon-based electrodes with graphene modification.

Referring to FIG. 8, a general process is stated for graphene layer formation. It starts with an ink where at least one component comprises graphene platelets. Then a deposition method is applied to a surface or substrate. Next, a possible drying phase is performed to evaporate the solvent. Finally, the assembly is subjected to post-processing, which may include, but is not limited to, various chemical, biological, or physical treatments.

For example, one may use a commercial inkjet printer from Dimatix to apply the graphene layer in a very controlled fashion. The typical drop volume from the printer cartridge can be around 1 pL, so the drop size is approximately 1 μm. Such a fine mist allows accurate control of the surface thickness to the nano-scale. This control is in contrast to conventional screen printing whereby, the ink is pushed through a metal mesh to make a several hundred micron thick ink layer that later is dried. After the curing process, such a procedure produces typical surface roughness on the order of several microns as opposed to nanometers when using inkjet.

Fifth Embodiment

Electrochemical Activation

For the fifth embodiment, a carbon-based electrode may be electrochemically activated before, after and/or during graphene modification. Electrochemical activation may be used to increase the uniformity and reproducibility of carbon-based electrodes, and may employ measurement of electrochemical capacitance (e.g., because this value may increase as more electrochemically active surface groups are introduced during a given activation process, and the activation process may be allowed to continue until a target degree of activation is met, which may be some predefined electrode capacitance value).

For example, a carbon-based electrode modified with graphene according to embodiments of the present invention may be exposed to an aqueous solution, and a potential may be applied to the sensor in the cyclic manner. After application of activation potential (Vact) versus the potential of the reference electrode for a certain period (Tact), the potential may be brought back down to the value (Vcontrol) where the sensor does not normally participate in faradic reactions with electrolyte, and the controlling capacitance measurement is performed. After remaining at this potential for a predefined amount of time (Twait), a small sine wave may be superimposed around Vcontrol for a time that would be necessary enough to measure the capacitance (Tmeasure). For a given measurement, both sensor potential V(t) and current I(t) may be recorded, and at the end of each cycle the last sine wave may be analyzed and its amplitude Iampl, offset Iofst, and phase shift ($\phi$) between voltage and current may be calculated. The capacitance may then be estimated by the following equation:

$$C = I_{ampl}/V_{ampl} \cdot 2 \cdot \pi \cdot f \cdot \sin(\phi) \qquad \text{EQ. 1}$$

where Vampl is the amplitude of the applied potential wave, and f is the frequency.

The activation cycle may be ended when the capacitance becomes greater or equal to some predefined target value Cfinal.

In certain sample embodiments of the present invention, preferred values of the parameters mentioned above may be set but not limited to Vact=1.5 V, Tact=1 sec, Vcontrol=0.2 V, Twait=2 sec, Tmeasure=2 sec, f=10 Hz, Vampl=0.015 V.

The present invention has been described above with reference to preferred features and embodiments. Those skilled in the art will recognize, however, that changes and modifications may be made in these preferred embodiments without departing from the scope of the present invention. For example, those skilled in the art will recognize that although exemplary embodiments have been described above with respect to carbon-based electrodes, the present invention is also applicable to electrodes comprising other conductive materials (e.g., gold, platinum, palladium, etc.).

What is claimed is:

1. A method, comprising:
   forming a first electrochemical sensor electrode having an electrochemical capacitance value less than a pre-defined electrochemical capacitance target value;
   exposing the first electrochemical sensor electrode to an electrochemically active substance, and during the exposure:
      applying a first potential to the first electrochemical sensor electrode;
      raising the first potential to an activation potential for an activation period of time;
      reducing the first potential to a control potential for a control period of time;
      measuring a first electrochemical capacitance of the first electrochemical sensor electrode; and
      repeating a first cyclic process of raising the first potential to the activation potential for the activation period of time, reducing the first potential to the control potential for the control period of time, and measuring the first electrochemical capacitance of the first electrochemical sensor electrode until the measured electrochemical capacitance equals or exceeds the pre-defined electrochemical capacitance target value.

2. The method of claim 1, further comprising:
forming a second electrochemical sensor electrode having an electrochemical capacitance value less than the pre-defined electrochemical capacitance target value;
exposing the second electrochemical sensor electrode to the electrochemically active substance;
applying a second potential to the second electrochemical sensor electrode;
raising the second potential to the activation potential for the activation period of time;
reducing the second potential to the control potential for the control period of time;
measuring a second electrochemical capacitance of the second electrochemical sensor electrode; and
repeating a second cyclic process of raising the second potential to the activation potential for the activation period of time, reducing the second potential to the control potential for the control period of time, and measuring the second electrochemical capacitance of the second electrochemical sensor electrode until the measured electrochemical capacitance equals or exceeds electrochemical capacitance target value.

3. The method of claim 2, wherein the first electrochemical sensor electrode and the second electrochemical sensor electrode are carbon-based.

4. The method of claim 3, wherein forming the first electrochemical sensor electrode comprises depositing a first layer of graphene on a first carbon sensing pad, and wherein forming the second electrochemical sensor electrode comprises depositing a second layer of graphene on a second carbon sensing pad.

5. The method of claim 4, wherein measuring the first electrochemical capacitance of the first electrochemical sensor electrode comprises superimposing on the first potential a sine wave around the control potential, and wherein measuring the second electrochemical capacitance of the second electrochemical sensor electrode comprises superimposing on the second potential the sine wave around the control potential.

6. The method of claim 5, further comprising attaching at least one of antibodies and DNA to the first layer of graphene and the second layer of graphene.

7. The method of claim 6, wherein depositing the first layer of graphene on the first carbon sensing pad is performed before measuring the first electrochemical capacitance of the first electrochemical sensor electrode, and wherein depositing the second layer of graphene on the second carbon sensing pad is performed before measuring the second electrochemical capacitance of the second electrochemical sensor electrode.

8. The method of claim 7, wherein depositing the first layer of graphene on the first carbon sensing pad is performed after measuring the first electrochemical capacitance of the first electrochemical sensor electrode, and wherein depositing the second layer of graphene on the second carbon sensing pad is performed after measuring the second electrochemical capacitance of the second electrochemical sensor electrode.

9. The method of claim 1, wherein forming the first electrochemical sensor electrode comprises depositing a first layer of graphene on a first carbon sensing pad, and wherein forming the second electrochemical sensor electrode comprises depositing a second layer of graphene on a second carbon sensing pad.

10. The method of claim 1, further comprising attaching at least one of antibodies and DNA to the first electrochemical sensor electrode and the second electrochemical sensor electrode.

11. The method of claim 1, wherein the first sensor electrode is carbon-based.

12. The method of claim 11, wherein forming the first sensor electrode comprises depositing a layer of graphene on a carbon sensing pad.

13. The method of claim 12, wherein measuring the electrochemical capacitance of the first sensor electrode comprises superimposing on the potential a sine wave around the control potential for a period of time sufficient to measure the electrochemical capacitance of the first sensor electrode.

14. The method of claim 13, further comprising attaching at least one of antibodies and DNA to the layer of graphene.

15. The method of claim 14, wherein depositing the layer of graphene on the carbon sensing pad is performed before exposing the first sensor electrode to an electrochemically active substance.

16. The method of claim 14, wherein depositing the layer of graphene on the carbon sensing pad is performed after the measured electrochemical capacitance of the first sensor electrode equals or exceeds the pre-defined electrochemical capacitance target value.

17. The method of claim 1, wherein measuring the electrochemical capacitance of the first sensor electrode comprises superimposing a sine wave around the control potential for a period of time sufficient to measure the electrochemical capacitance of the first sensor electrode.

18. The method of claim 1, wherein forming the first sensor electrode comprises depositing a layer of graphene on a carbon sensing pad.

19. The method of claim 1, further comprising attaching at least one of antibodies and DNA to the first sensor electrode.

* * * * *